(12) United States Patent
Johnson

(10) Patent No.: US 6,251,295 B1
(45) Date of Patent: Jun. 26, 2001

(54) METHOD FOR RECIRCULATION WASHING OF BLOOD CELLS

(75) Inventor: Craig L. Johnson, Mission Viejo, CA (US)

(73) Assignee: Nexell Therapeutics Inc., Irvine, CA (US)

(*) Notice: Subject to any disclaimer, the term of this patent is extended or adjusted under 35 U.S.C. 154(b) by 0 days.

(21) Appl. No.: 09/004,344

(22) Filed: Jan. 8, 1998

(51) Int. Cl.[7] .............................. B01D 61/14; A61M 1/34
(52) U.S. Cl. .......................... 210/805; 210/650; 210/651; 210/780; 210/782; 604/4.01; 604/5.01
(58) Field of Search ......................... 210/650, 651, 210/805, 321.67, 321.68, 780, 195.3, 194, 782, 787; 604/4, 5, 6, 4.01, 5.01; 436/177, 178; 435/297.1, 297.3, 2, 7.1

(56) References Cited

U.S. PATENT DOCUMENTS

| Re. 26,006 | 4/1966 | Gewecke . |
| 2,704,544 | 3/1955 | Ryan . |
| 4,102,655 | 7/1978 | Jeffery et al. . |
| 4,675,106 | 6/1987 | Schoendorfer et al. . |
| 4,753,729 | 6/1988 | Schoendorfer et al. . |
| 4,816,151 | 3/1989 | Schoendorfer et al. . |
| 4,886,487 * | 12/1989 | Solem et al. ........................ 604/5 |
| 4,943,288 * | 7/1990 | Kurtz et al. ...................... 604/408 |
| 4,976,707 | 12/1990 | Bodicky et al. . |
| 4,980,054 * | 12/1990 | Lavender ............................... 210/90 |
| 5,034,135 | 7/1991 | Fischel . |
| 5,053,121 | 10/1991 | Schoendorfer et al. . |
| 5,055,198 * | 10/1991 | Shettigar ............................ 210/104 |
| 5,194,145 | 3/1993 | Schoendorfer . |
| 5,215,519 * | 6/1993 | Shettigar ................................ 604/4 |
| 5,234,608 | 8/1993 | Duff . |
| 5,298,016 | 3/1994 | Gordon . |
| 5,460,493 * | 10/1995 | Deniega et al. ................. 417/477.2 |
| 5,536,475 | 7/1996 | Moubayed et al. . |
| 5,580,349 * | 12/1996 | Thor et al. ......................... 604/406 |
| 5,649,903 * | 7/1997 | Deniega et al. .................. 604/4.01 |
| 5,695,489 | 12/1997 | Japuntich . |
| 5,762,791 * | 6/1998 | Deniega et al. ................ 210/321.67 |
| 5,876,611 * | 3/1999 | Shettiger ............................ 210/739 |

FOREIGN PATENT DOCUMENTS 2 117 101    10/1983   (GB) .

* cited by examiner

Primary Examiner—John Kim
(74) Attorney, Agent, or Firm—Oppenheimer Wolff & Donnelly LLP

(57) ABSTRACT

A bag or reservoir for recirculation washing of blood cells has a top outlet port and bottom inlet port. A method of recirculation washing of blood cells uses the bag in conjunction with a spinning membrane filter. The method can be used in an instrument for magnetic cell selection or a stand-alone cell washing apparatus.

33 Claims, 3 Drawing Sheets

METHOD FOR RECIRCULATION WASHING OF BLOOD CELLS

BACKGROUND OF THE INVENTION

This invention relates to recirculation washing of blood cells using a spinning membrane filter, and in particular to recirculation washing of blood cells in a magnetic cell selection apparatus.

Fischel U.S. Pat. No. 5,034,135, issued Jul. 23, 1991, and Schoendorfer U.S. Pat. No. 5,053,121, issued Oct. 1, 1991 disclose spinning membrane filters comprising a cylindrical housing and concentric grooved cylindrical rotor. The rotor is covered with a membrane the membrane is spaced from the inner wall of the housing. Blood is introduced into the gap between the membrane and housing. Filtrate passes through the membrane, into the grooves of the rotor, into tubes which communicate with the grooves, and out the bottom center of the spinning membrane filter. Concentrated cells are removed from the gap. FIGS. 7 and 8 in the Fischel patent illustrate a cell washing modification in which a porous wall is interposed between the membrane and the inner wall of the housing. Blood is introduced into the gap between the membrane and the porous wall and an isotonic wash solution is introduced into the gap between the porous wall and the inner wall of the housing. FIG. 6 in the Schoendorfer patent illustrates introduction of a rinse solution with the blood. Schoendorfer et al. U.S. Pat. No. 5,035,121, issued Oct. 1, 1991, discloses use of two spinning membrane filters in series or parallel. A washing solution is introduced into at least one of the spinning membrane filters.

Duff U.S. Pat. No. 5,234,608, issued Aug. 10, 1993, discloses a spinning membrane filter of the type which is preferred for use in conjunction with this invention. According to the disclosure, cell-rich concentrate is removed from the upper portion of the gap between the membrane and the inner wall of the housing, cell-poor plasma filtrate is removed from the bottom center of the spinning membrane filter. Source cell suspension is mixed with cell-rich concentrate and introduced to the lower portion of the gap area.

Schoendorfer et al. U.S. Pat. No. 4,675,106, issued Jun. 23, 1987, U.S. Pat. No. 4,753,729, issued Jun. 28, 1988, and U.S. Pat. No. 4,816,151, issued Mar. 28, 1989, disclose drive mechanisms for spinning membrane filters.

Moubayed et al. U.S. Pat. No. 5,536,475 discloses a semi-automated instrument for selection of blood cells using paramagnetic beads which are coated with a binding agent such as an antibody which binds specifically to the cells to be selected. The instrument comprises a primary magnet associated with a primary container and a secondary magnet associated with a secondary container. Blood cells, liquid and beads are agitated in the primary container to form a conjugate between the beads and the selected cells. The primary magnet is then moved into a position adjacent the primary container to magnetically capture the bead/cell conjugate and the non-selected cells and liquid are removed. The primary magnet is then moved into a position away from the primary container to release the bead/cell conjugate. Wash solution is added and the contents of the primary container are agitated, then the primary magnet is moved into the position adjacent the primary container to again capture the bead/cell conjugate and the wash solution is removed. The primary magnet is again moved into a position away from the primary container to release the bead/cell conjugate. Liquid containing a reagent which releases the selected cells from the beads is added and the contents are again agitated. The primary magnet is again moved into the position adjacent the primary container to capture the beads. The released cells and liquid are introduced to the secondary container. The secondary container is positioned adjacent to the secondary magnet to capture any beads which may have escaped the primary magnet. The instrument is used with a disposable set comprising plastic bags for wash liquid, cell suspension and bead suspension, interconnected with plastic tubing.

The semi-automated instrument disclosed in the Moubayed et al. patent is sold by Baxter Healthcare Corporation, under the trademark Isolext® 300 SA. A modified version of the instrument is sold by the Baxter Healthcare Corporation under the trademark Isolex® 300i. The 300i differs from the 300 SA in that it is fully automated and it includes a spinning membrane filter for washing the selected cells and also for removing platelets from the source cells prior to selection.

Chapman et al. International Publication WO 95/13837, published May 26, 1995, discloses a peristaltic pumping assembly of a type which is used to move fluids in the Isolex® 300 SA and Isolex® 300i instruments. Deniega et al. International Publication WO 95/14172, published May 26, 1995, discloses an organizer frame of a type which is used with the peristaltic pumping assembly in the Isolex® 300 SA and Isolex® 300i instruments. The organizer frame is also used on a machine for separation of platelets from whole blood. Deniega discloses a tubing set which includes a spinning membrane filter and a reservoir for platelet-poor packed blood cells. The reservoir has a top and bottom port. Packed cells from the outlet of the spinning membrane filter enter through the top inlet port of the reservoir. Whole blood from a patient enters through the bottom inlet port.

Recirculation washing of selected blood cells is performed in the Isolex® 300i utilizing the spinning membrane filter in conjunction with a recirculation wash bag which has both inlet and outlet ports at the bottom and no port at the top. The bag is a 600 ml bag with the inlet and outlet ports separated by about 2 inches. The bag has been able to concentrate cell suspensions that normally start at about 400 ml. This bag performed better when it was occasionally massaged. This is the only way to process more than about $5 \times 10^{10}$ cells in the bag.

The above-cited U.S. patent and International Publications are each incorporated herein by reference.

SUMMARY OF THE INVENTION

This invention includes a method, a bag and a disposable set for recirculation washing of blood cells. The invention can be used for washing of blood cells in a magnetic cell selection instrument, but can also be used for washing whole blood or other blood cell products.

The recirculation wash bag is a flexible plastic bag which has a top port and a bottom port. In one embodiment, an integral coarse filter comprising a tube of semi-rigid plastic mesh extends from the top port into the bag. This filter provides mild resistance to larger cell aggregates. In another embodiment, the bag includes a bubble trap at the top comprising tubing extending into the bag from the top port. In the preferred embodiment, the bag includes both the semi-rigid integral filter and the bubble trap; the tubing for the bubble trap fits inside the plastic mesh tube to provide a space to accumulate air around the tubing. When a system incorporating the bag is primed with buffer solution, vacuum is pulled on the bag. Because the filter is semi-rigid, it holds open a path through the otherwise collapsed bag for the cells to move up to the top port.

The method of the invention utilizes a flexible plastic recirculation wash bag and a spinning membrane filter. The spinning membrane filter has an inlet port for a diluted suspension of blood cells in buffer solution, a first outlet port for filtrate, and a second outlet port for a concentrated suspension of blood cells in buffer solution. The recirculation wash bag has a top outlet port and a bottom inlet port. Preferably, the recirculation wash bag includes the integral coarse filter and bubble trap described above.

The method comprises withdrawing a suspension of blood cells in buffer solution from the recirculation wash bag through the top port, mixing the suspension with additional buffer solution to form a diluted suspension of blood cells in buffer solution, feeding the diluted suspension into the spinning membrane filter through the inlet port, withdrawing filtrate comprising buffer solution from the spinning membrane filter through the first outlet port, withdrawing a concentrated suspension of blood cells in buffer solution from the spinning membrane filter through the second outlet port, feeding the concentrated suspension into the bag through the bottom port, and continuing the recirculation washing until the desired amount of washing has been achieved. A method for determining when the desired amount of washing has been achieved, based on an estimate of "residual," is described below. The residual represents the target component for reduction (e.g., platelets, antibody, etc., as described below).

In one embodiment of the method, the suspension of blood cells withdrawn through the top port of the recirculation wash bag is mixed with unwashed blood cells as well as buffer solution before feeding the diluted suspension into the spinning membrane filter. In one aspect of this embodiment, the unwashed blood cells include platelets, the filtrate comprises a suspension of platelets in buffer solution, and the recirculation washing is continued until the platelet content of the concentrated suspension of cells has been reduced to the desired level.

In another embodiment of the method, the recirculation wash bag at the beginning of the recirculation wash procedure contains, in addition to blood cells, an antibody which specifically binds an antigen on certain of the blood cells, the filtrate comprises a suspension of the antibody in the buffer solution, and the recirculation washing continues until the concentrated suspension of cells contains the desired amount of excess, unbound antibody.

In another embodiment of the method, the recirculation wash bag at the beginning of the recirculation wash procedure contains blood cells which have been selected in a magnetic cell selection procedure and a peptide release agent which was used to release the selected cells from a cell/magnetic bead conjugate, the filtrate comprises a solution of the peptide release agent in buffer solution, and the recirculation washing is continued until the peptide release content of the concentrated suspension of cells has been reduced to the desired level.

The disposable set of the invention comprises the recirculation wash bag and the spinning membrane filter having ports as described above, and a filtrate bag, plus associated tubing, including tubing for a buffer solution bag. Plastic tubing connects the top port of the recirculation wash bag to a mixing zone. Plastic tubing with a buffer bag spike coupler at one end is connected to the same mixing zone. The mixing zone is connected by plastic tubing to the inlet port of the spinning membrane filter. The first outlet port of the spinning membrane filter is connected by plastic tubing to the inlet port of the filtrate bag. The second outlet port of the spinning membrane filter is connected by plastic tubing to the bottom port of the recirculation wash bag.

The disposable set may also include other bags and associated tubing for use in a magnetic cell selection instrument, such as a bag for antibody suspension in buffer solution, a bag for peptide release agent solution in buffer solution, a bag for a suspension of the nonselected cells in buffer solution, and an end product bag for washed cells. A bag for unwashed cells (also referred to as a cell source bag) and/or a bag for buffer solution may be included in the set, but in the preferred embodiment these items are supplied separately.

Use of a flexible recirculation wash bag with ports at the top and bottom and flow from bottom to top provides several advantages as compared to a bag with inlet and outlet ports at the bottom, as currently used on the Isolex® 300i. First, using a flexible bag allows the volume to be varied depending on the number of cells. Exiting from the top has the advantage of removing the less dense supernatant preferentially. This aids in making the concentration ratio high. (The importance of high concentration ratio is discussed below). For large volumes or slow flow rates, some sedimentation of the larger cells also aids in reducing the cell concentration at the outlet port. The system has the advantage of having the most washed and most concentrated cells at the bottom with the least washed and least concentrated cells at the top. Additional advantages include the following: (1) allows accurate residual estimates which in turn allow optimal residual levels instead of just reduction; (2) provides more uniform processing of cells which leads to a more uniform product for the selection process; (3) manual massaging of the bag during the wash is not required, permitting hands-free operation.

DETAILED DESCRIPTION OF THE INVENTION

Figure 1:
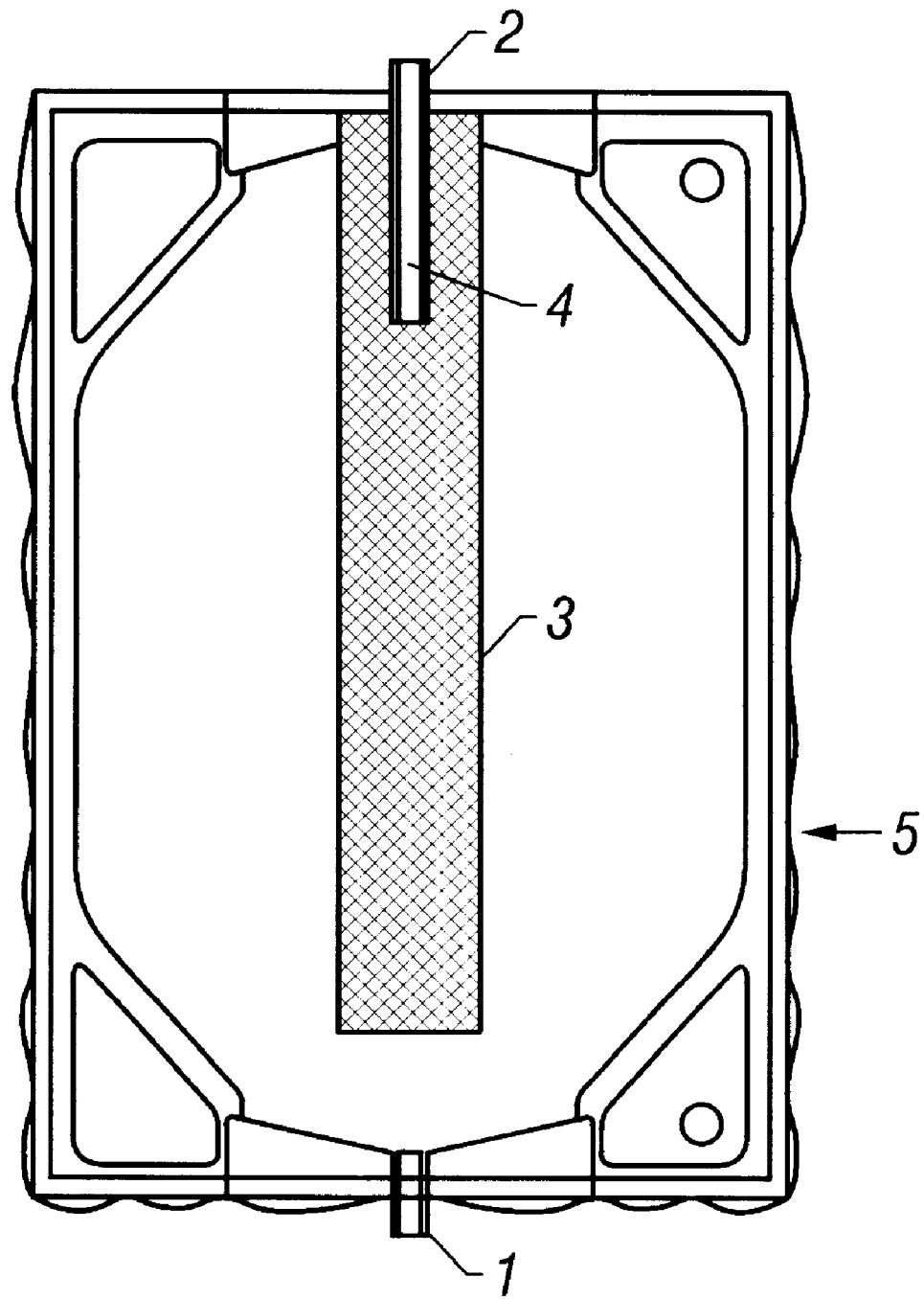
FIG. 1 illustrates the preferred embodiment of the recirculation wash bag of this invention. In the description which follows the recirculation wash bag having the configuration shown in FIG. 1 is referred to as the IsoFlow™ bag.

IsoFlow™ recirculation wash bag Referring to FIG. 1, the IsoFlow™ bag is indicated generally by the numeral 5. The bag is made of a flexible plastic such as and includes bottom port 1 and top port 2. An integral coarse filter comprising a tube of semi-rigid plastic mesh 3 extends from the top port into the bag to within about ½ to 3 inches, preferably about 1 inch, from the bottom of the bag. The mesh tube is about ½ to about 1.5 inches in diameter, preferably about 1 inch in diameter, and is preferably closed at its lower end. The tube's mesh (opening) size is in the range of about 80–400 microns, preferably about 230 microns. The bag includes a bubble trap at the top which is created by inserting tubing 4 into the top port about ½ to 3 inches, preferably about 1.5 inches. Suitable materials of construction include polyvinyl chloride (PVC) for the bag, polyester (e.g. Cleartuf®, shell) for the mesh tube filter, and PVC for the tubing. Volume of the bag can vary, but will generally be between 100 and 1500 ml. As presently designed for use on the Isolex® 300i, the bag holds a volume of 400 ml. The mesh could be replaced by some other semi-rigid, rigid or combination structure that facilitates flow from bottom to top.

Isolex® 300i cell washing system

Figure 2:
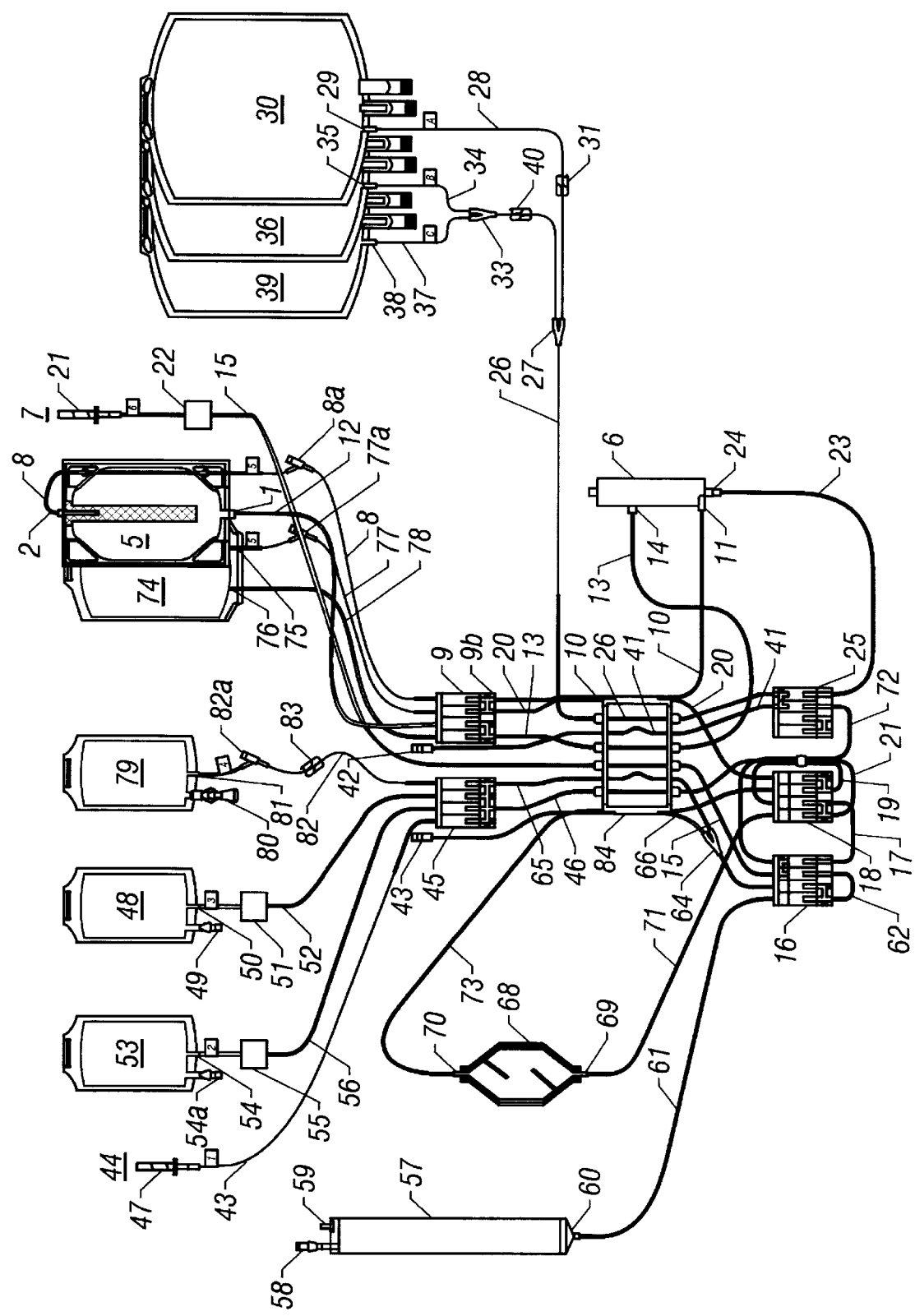
FIG. 2 illustrates a disposable set of this invention which is adapted for use on a magnetic cell selection device such as the Isolex® 300i.

Referring to FIG.2, the disposable set of this invention comprises the, IsoFlow™ bag 5 and spinning membrane filter 6 and associated tubing, including tubing for connecting a bag containing buffer solution. Spinning membrane filter 6 (sometimes referred to simply as "spinning membrane" or "spinner") has the construction shown in FIG. 2 of Duff U.S. Pat. No. 5,234,608. The membrane is a nominal 4 micron polycarbonate membrane. The buffer solution bag is not shown, but is indicated at 7; it is a standard flexible plastic bag with a bottom outlet port, and is supplied separately. The top port 2 of IsoFlow™ bag 5 is connected by tubing 8 having a sampling device 8a to the bottom right channel 9b (indicated by dotted lines) of clamp manifold 9. Channel 9b is a mixing zone for mixing cells from IsoFlow™ bag 5 with buffer solution from bag 7 and (in the platelet separation step described below) with unwashed cells from bag 44. Channel 9b of clamp manifold 9 is connected by tubing 10 to the inlet port 11 of spinning membrane filter 6. The bottom port 1 of IsoFlow™ bag 5 is connected by tubing 12 to the bottom left channel of clamp manifold 9 and tubing 13 connects the bottom left channel of clamp manifold 9 to the outlet port 14 of spinning membrane filter 6. Tubing 15 connects the outlet port of buffer solution bag 7 to the top right channel of clamp manifold 16; tubing 17 connects the top right channel of clamp manifold 16 to the bottom left channel of clamp manifold 18; tubing 19 connects the bottom left channel of clamp manifold 18 to the bottom right channel of clamp manifold 18 and tubing 20 connects the bottom right channel of clamp manifold 18 to the bottom right channel 9b of clamp manifold 9. Tubing 15 is connected to a buffer bag spike coupler 21 and a sterilizing filter 22. Tubing 23 connects filtrate outlet port 24 of spinning membrane filter 6 with the top right channel of clamp manifold 25. Tubing 26 connects the top right channel of clamp manifold 25 with Y-connector 27. Tubing 28 connects Y-connector 27 to the inlet port 29 of filtrate (waste) bag 30. On tubing 28 is a clamp 31. Tubing 32 connects Y-connector 27 to Y-connector 33. Tubing 32 carries a clamp 40. Tubing 34 connects Y-connector 33 to inlet port 35 of waste bag 36. Tubing 37 connectes Y-connector 33 to inlet port 38 of waste bag 39. Tubing 41 connects the top right channel of clamp manifold 25 to pressure transducer protector 42.

There are three configurations of clamp manifolds shown in FIG. 2. All configurations have clamps capable of obstructing the tubing that runs through them on a flat platen (not shown) in the center of the manifolds. The dotted lines in the upper and/or lower portions of the clamp manifolds indicate the locations of channels within the manifolds. The dotted lines in clamp manifold 45 show that the bottom channel connects all 4 tubes. The dotted lines in clamp manifolds 9 and 18 show that there are two bottom channels—the left channel connects the two left tubes and the right bottom connects the two right tubes. The dotted lines in clamp manifolds 16 and 25 show that the bottom left channel connects the tubes on the left and the top right channel connects the tubes on the right.

In the preferred embodiment illustrated in FIG. 2, the disposable set of the invention also includes other bags and containers and associated tubing adapted for use on a magnetic cell separation instrument such as the the Isolex® 300i. Tubing 43 connects a cell source bag (not shown, but indicated at 44) with the bottom channel of clamp manifold 45. Tubing 46 connects the bottom channel of clamp manifold 45 with the bottom left channel 18a of clamp manifold 18. Channel 18a is a mixing zone for buffer from bag 7 and unwashed cells from bag 44. Tubing 43 is connected to a starting cells spike coupler 47.

Bag 48 is a bag for antibody which reacts specifically with cells to be selected on the Isolex® 300i. For example, where CD34+ cells are to be selected, bag 48 will contain anti-CD34 antibody. The bag has an injection site 49 for injection of the antibody solution and an outlet port 50 connected to a sterilizing filter 51. Tubing 52 connects sterilizing filter 51 to the bottom channel of clamp manifold 45.

Bag 53 is a bag for a peptide release agent which displaces the antibody from the cells after the cells have been magnetically selected. Bag 53 has an injection site 54a for injection of a solution of the peptide and an outlet port 54 connected to a sterilizing filter 55. Tubing 56 connects sterilizing filter 55 to the bottom channel of clamp manifold 45.

Cylinder 57 is the primary magnet separation chamber. It has a vent filter 59 and an injection site 58 for injection of paramagnetic microbeads coated with an antibody which binds specifically to the antibody in bag 48. It has a bottom port 60 which serves as both inlet and outlet for cell suspensions. In use it is mounted on a rocker mechanism as described in Moubayed et al. U.S. Pat. No. 5,536,475. Port 60 is connected by tubing 61 to the bottom left channel of clamp manifold 16. That channel is connected by tubing 62 to the right top channel of clamp manifold 16. The top right channel of manifold 16 is connected by tubing 72 to the top right chamber of clamp manifold 25. The bottom left channel of clamp manifold 16 is also connected by tubing 63 to Y-connector 64 and the latter is connected by tubing 65 to the bottom channel of clamp manifold 45. Y-connector 64 is also connected by tubing 66 to a pressure transducer protector 67.

Bag 68 is the secondary magnet separation bag described in Moubayed et al. U.S. Pat. No. 5,536,475. It has inlet port 69 and outlet port 70. Inlet port 69 is connected by tubing 71 to the bottom left channel of clamp manifold 18. Outlet port 70 is connected by tubing 73 to the bottom right channel of clamp manifold 18.

Bag 74 is a selected cell wash bag. It has two bottom ports. Inlet port 75 is connected by tubing 77 which has a sampling device 77a to the bottom right channel 9b of clamp manifold 9. Outlet port 76 is connected by tubing 78 to the bottom left channel of clamp manifold 9. If desired, an IsoFlow™ bag can be substituted for the selected cell wash bag.

Bag 79 is an end product bag. It has an injection site 80 and an inlet port 81. Tubing 82 carrying sampling device 82a and clamp 83 connects inlet port 81 with the bottom channel of clamp manifold 45.

Frame 84 is an organizer frame as described in Denieaga et al. International Publication WO 95/14142 for use with a peristaltic pump assembly (not shown) as described in Chapman et al. International Publication WO 95/13837. Tubing 13, 15, 26 and 46 each passes through one of the four pumping modules of the peristaltic pump assembly.

The volume of bags can vary, depending upon the volume of cells to be processed. In the commercial Isolex® 300i instrument, each of bags 30, 36 and 39 has a volume of 2000 ml, each of bags 48, 53 and 79 has a volume of 150 ml, and bag 74 has a volume of 600 ml. For use in this system, the IsoFlow™ bag 5 has a volume of 400 ml.

At the beginning of a cell selection procedure, the disposable set of FIG. 2 is placed on the Isolex 300i. Bag 7 containing buffer and bag 44 containing source cells are attached. The source cells are typically a leukapheresis product from a cell separation device such as a Fenwall 3000 CS. The buffer bag has a capacity of 4000 ml and a starting volume of at least 3500 ml. The cell source bag has a capacity of 1000 ml and a starting volume of about 500 ml. By appropriate operation of clamps in the clamp manifolds and the pumps on tubing 13, 15, and 46, buffer solution is added to the following elemments and connecting tubing to prime the system: Isoflow™ bag 5, secondary magnet pouch 68, spinning membrane filter 6, filtrate bag 30, selected cell wash bag 74, release agent bag 53, antibody bag 48, cell source bag 44. During the prime, fluid is added to the Isoflow™ bag, the air is removed from the top part of the bag, more fluid is added through the bottom part, and excess air is released through tubing 8 to waste bag 30.

At this point the system is ready for removal of platelets from the leukapheresis product in cell source bag 44, using the method of this invention. For purpose of the following description: clamps in clamp manifold 45 are designated clamps C1, C2, C3, C4; clamps in clamp manifold 9 are designated C5, C6,C7, C8; clamps in clamp manifold 16 are designated C9, C10, C11, C12; clamps in clamp manifold 18 are designated C13, C14, C15, C16; clamps in clamp manifold 25 are designated C17, C18, C19, C20; the pump on tubing 46 is designated P1, the cell source pump; the pump on tubing 15 is designated P2, the buffer pump; the pump on tubing 13 is designated P3, the recirculation pump; the pump on line 26 is designated P4, the filtrate pump; and the rotor of spinning membrane filter 6 is designated as pump P5.

Prior to beginning cell wash, clamps C6, C8, C10, C11, C12, C14, C16 and C20 are opened, pumps P2, P3, P4 and P5 are moving. This circulates buffer solution from bag 7, into the inlet port 11 and out of outlet ports 14 and 24 of spinning membrane filter 6, into bottom port 1 and out of top port 2 of IsoFlow™ bag 5, and into filtrate bag 30.

To conduct recirculation washing of the blood cells for platelet removal, clamps C1, C6, C8, C12, C14, C16 and C20 are open, pumps P1, P2, P3, P4, and P5 are moving. A suspension of unwashed blood cells is withdrawn from cell source bag 44 through tubing 43 to the bottom channel of clamp manifold 45, then out through tubing 46 to the bottom left channel 18a of clamp manifold 18 where it is mixed with buffer solution. The buffer solution is withdrawn from buffer bag 7 through tubing 15 to the top right channel of clamp manifold 16, then out through tubing 17 to the bottom left channel 18a of clamp manifold 18. The diluted suspension of blood cells in buffer solution flows out of the bottom left channel 18a through tubing 19 into the bottom right channel of clamp manifold 18, then out through tubing 20 to the bottom right channel 9b of clamp manifold 9, where it is mixed with additional buffer solution from top port 2 of Isoflow™ bag 5. The diluted suspension of blood cells in buffer solution flows from channel 9b through tubing 10 to the inlet port 11 of spinning membrane filter 6. Platelets, a few red cells, and buffer flow through the membrane and out through outlet port 24 through tubing 23 to the top right channel of clamp manifold 25, then out through tubing 26 and 28 to filtrate bag 30 (clamp 31 open, clamp 40 closed). (The nominal 4 micron membrane used removes about 95% of platelets from a leukapheresis product, while about 50% of red cells are also removed.) A concentrated suspension of blood cells in buffer flows from the exit port 14 of spinning in membrane filter 6 through tubing 13 to the bottom left channel of clamp manifold 9, then out through tubing 12 through the bottom port 1 into Isoflow™ bag 5. As the process continues, a suspension of blood cells in buffer solution flows out of the top of the Isoflow™ bag 5. These cells are mixed in mixing zone 9b with unwashed cells from source bag 44 and are recirculated through the spinning membrane filter 6. Recirculation washing is continued until the desired level of platelet removal has been achieved.

After platelet removal, antibody in buffer solution is transferred to the concentrated suspension of blood cells in buffer solution in the Isoflow™ bag 5. For transfer of antibody solution from bag 48 to Isoflow™ bag 5, clamps C3, C6, C8, C14, C16 and C20 are open and pumps P1, P3 and P5 are moving. The antibody and cells are mixed in mixing zone 9b. Then the antibody tubing is rinsed with buffer solution while the antibody/cell suspension circulates through the Isoflow™ bag 5 and spinning membrane filter 6. This occurs with clamps C6, C8, C10, C11, C14, C16 and C20 open,and with pumps P1, P2, P3 and P5 moving. Next the antibody/cell suspension is circulated through the Isoflow™ bag 5 and spinning membrane filter 6 to sensitize the cells by binding with the antibody. This is accomplished with clamps C6, C8 and C20 open, and with pumps P3 and P5 moving.

After the cells have been sensitized by binding with antibody, they are washed to remove excess unbound antibody using the method of this invention. With clamps C6, C8, C12, C14, C16 and C20 open and with pumps P2, P3, P4 and P5 moving, a suspension of blood cells in buffer solution and containing excess unbound antibody is withdrawn from Isoflow™ bag 5 through top port 2 and flows through tubing 8 to the mixing zone 9b in clamp manifold 9. Buffer solution is withdrawn from buffer bag 7 through tubing 15, clamp manifold 16, tubing 17, clamp manifold 18 (left channel), tubing 19, clamp manifold 18 (right channel) and tubing 20, as previously described, to mixing zone 9b, where it is mixed with the suspension of blood cells from Isoflow™ bag 5 to form a diluted suspension of blood cells containing excess unbound antibody. This diluted suspension flows through tubing 10 to inlet port 11 of the spinning membrane filter 6. Filtrate comprising antibody in buffer solution flows out of outlet port 24, through tubing 23, clamp manifold 25, tubing 26, tubing 28, and port 29 into filtrate bag 30. A concentrated suspension of blood cells in buffer solution flows from the outlet port 14 of the spinning membrane filter 6, through tubing 13, clamp manifold 9 (bottom left channel), tubing 12 and bottom port 1 into Isoflow™ bag 5. The recirculation washing is continued until the cell suspension contains the desired level of unbound antibody.

After antibody sensitization and removal of excess unbound antibody, the cells are transferred to primary magnet separation chamber 57. Antibody-coated paramagnetic microbeads are mixed with the cells to form a conjugate between the microbeads and the sensitized cells, the conjugate is magnetically separated from the non-sensitized cells, the non-sensitized cells are transferred to waste bag 36, peptide release agent from bag 53 is added to the chamber 57 to release the selected cells, the selected cells are transferred to the secondary magnet separation bag where any remaining microbeads are separated magnetically, and the selected cells are transferred to selected cell wash bag 74. The selected cells are then recirculation washed to remove excess peptide release agent using spinning membrane filter 6, all in conventional manner. If desired, selected cell wash bag can be an Isoflow™ bag, and the recirculation wash to remove peptide release agent can be conducted using the method of this invention. After removal of peptide release agent, the selected cells are transferred to end product bag 79.

Stand-alone Cell Washing System

Figure 3:
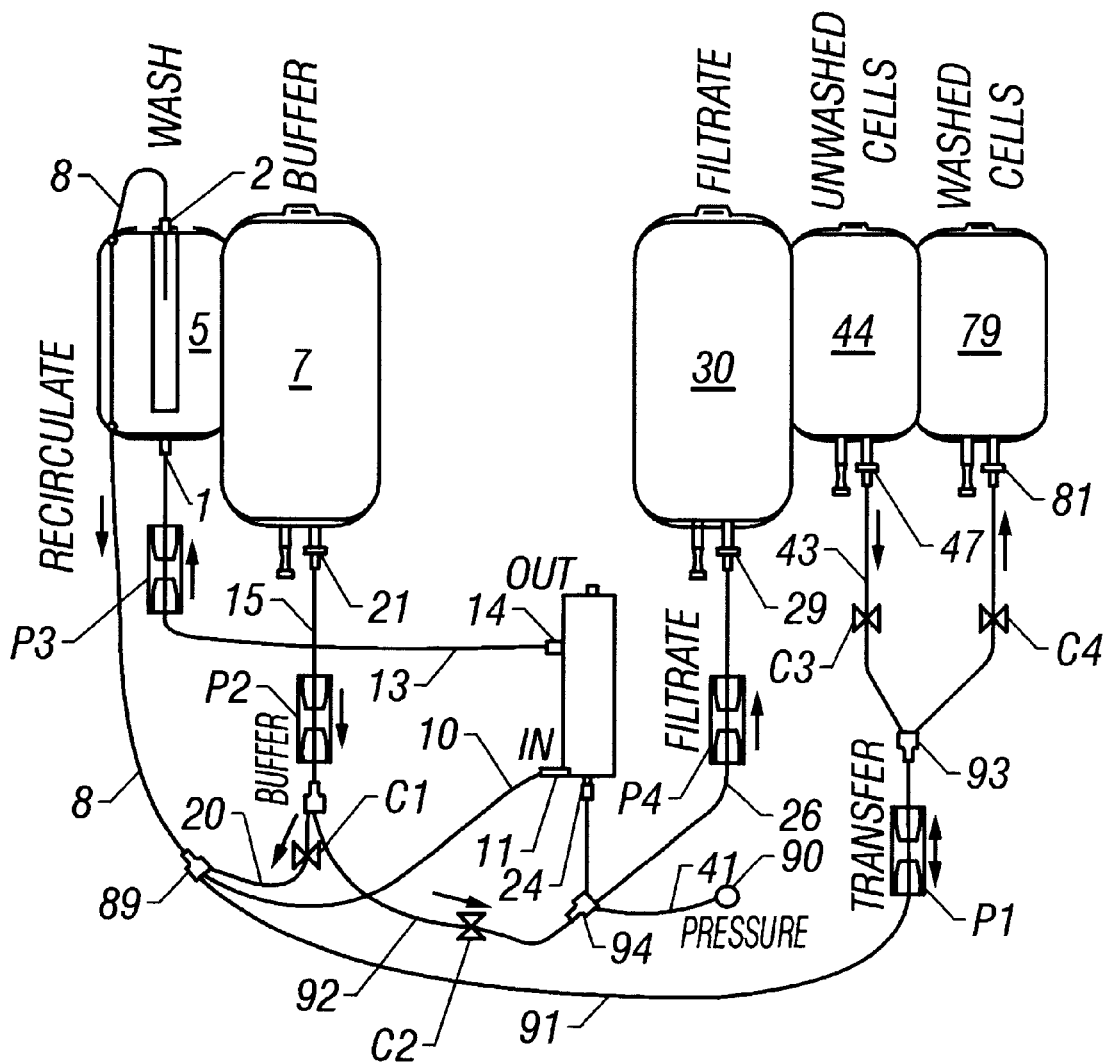
FIG. 3 illustrates a disposable cell wash set of the invention which is adapted for use on a stand-alone cell washing apparatus.

FIG. 3 illustrates a disposable set of the invention which is adapted for use on a stand-alone cell washing apparatus, i.e., an apparatus which does not include a cell selection function such as the magnetic cell selection of the Isolex® 300i instrument.

The disposable set includes Isoflow™ bag 5 having top port 2 and bottom port 1, spinning membrane filter 6 having inlet port 11 for a diluted suspension of blood cells, outlet port 14 for a concentrated suspension of blood cells, and outlet port 24 for filtrate, and filtrate bag 30 having inlet port 29. It may also include one or more of washed cell bag 79 having outlet port 81, unwashed cell bag 44 having outlet port 47, and buffer solution bag 7 having outlet port 21. Top port 2 of Isoflow™ bag 5 is connected by tubing 8 to connector 89. Port 21 of buffer bag 7 is connected by tubing 15 to Y-connector 95 and the latter is connected by tubing 20 carrying clamp C1 to connector 89. Port 47 of unwashed cell bag is connected by tubing 43 carrying clamp C3 to Y-connector 93 and then by tubing 91 to connector 89. Connector 89 serves as a mixing zone for unwashed cells in buffer solution from bag 44, recirculating cells in buffer solution from bag 5 and buffer solution from bag 7. Connector 89 is connected by tubing 10 to inlet port 11 of spinning membrane filter 6. Filtrate outlet port 24 of spinner 6 is connected by tubing 23 to Y-connector 94 and by tubing 26 to the inlet port 29 of filtrate bag 30. Connector 95 is connected by tubing 92 carrying clamp C2 to connector 94. Connector 94 is connected by tubing 41 to pressure transducer 90. Oulet port 14 of spinner 6 is connected by tubing 13 to the bottom port 1 of Isoflow™ bag 5. Y-connector 93 is connected by tubing 82 carrying clamp C4 to inlet port 81 of washed cell bag 79.

During recirculation washing, a suspension of blood cells in buffer solution is withdrawn from the Isoflow™ bag 5 through the top port 2 and flows through tubing 8 to mixing zone 89. Unwashed cells in buffer solution are withdrawn from bag 44 through port 47 and (with clamp C3 open and clamp C4 closed) through tubing 43 to Y-connector 93 and then through tubing 91 to mixing zone 89 by the transfer pump P2. Buffer solution is withdrawn from bag 7 through port 21 and tubing 15 to connector 95 by the buffer pump P2. With clamp C1 open, buffer flows through tubing 20 to mixing zone 89. A diluted suspension of blood cells in buffer solution flows from mixing zone 89 through tubing 10 to inlet port 11 of spinner 6. A concentrated suspension of blood cells in buffer solution flows through outlet port 14 of spinner 6 through tubing 13 and inlet port 1 into Isoflow™ bag 5 by recirculation pump P3. Filtrate flows through outlet port 24 in spinner 6 and tubing 23 to connector 94 and, with clamp C2 closed, through tubing 26 and inlet port 29 into filtrate bag 30 by pump P4. Recirculation washing is continued until the desired amount of target component has been removed from the blood cells. Clamps C1, C2 and C3 are then closed, clamp C4 is opened, and the direction of pump P1 is reversed, so that the suspension of washed cells flows from bag 5 through tubing 8, 91 and 82 and port 81 into washed cell bag 79. The lines, bag and spinner are then rinsed by closing clamps C1 and C3, opening clamps C4 and C2, and pumping buffer with pump P2 in series with pumps P1 and P3 to rinse the spinner, Isoflow™ bag and tubing.

System controls

In carrying out the recirculation washing method of this invention, the filtrate rate (f) is typically fixed at about 70 ml/min. During the transfer of cells into the wash circuit, the recirculation rate (r) provides the primary pressure regulation (using the concentration ratio CR described below) and varies from 14 to 70 ml/min. During the recirculation phase the recirculation rate ranges from about 24 to 70 ml/min. The buffer solution rate (b) ranges from 0 to 70 ml/min. to maintain a minimum scale volume and as a secondary pressure regulation mechanism. The rotor of the spinning membrane filter operates at a maximum of 3700 RPM and a minimum of about 2340 RPM during normal processing.

The Isolex® 300i system is automatically controlled using microprocessors. These microprocessors in-turn control 5 banks of 4 clamps each (clamps C1–C20), 1 bank of pumps (pumps P1–P4), 1 spinner motor drive P5 (drive for the rotor of spinning membrane filter 6), and 1 rocker assembly for container 57 with an integral magnet carriage to facilitate separation of magnetic beads (not shown, but described in Moubayed et al. U.S. Pat. No. 5,536,475). The system uses feedback from 6 weight scales (not shown), 2 pressure transducers (not shown, but attached to line 66 at 67 and to line 41 at 42, and 3 sets of fluid and tubing detectors (not shown but attached to lines 61, 66 and 41). During the Isolex® 300i procedure the bags 44, 53, 48 and 79 are hung on weight scales 1, 2, 3 and 4, respectively. Bags 74 and 5 are hung together on weight scale 5. Buffer bag 7 is hung on weight scale 5. Buffer bag 7 is hung on weight scale 6. Bags 36, 39 and 30 are not hung on a scale. Weight scale 5 is used to determine the cell product volume in the wash circuit by substracting out the reference weight when the Isoflow™ bag is empty. The weight scales are in the tower of the Isolex® 300i instrument.

The stand-alone cell washing system will also run automatically using microprocessors. These microprocessors in turn control 1 bank of 4 clamps each, 1 bank of 4 pumps and 1 spinner motor drive. The system will require feedback from 4 weight scales, 2 pressure transducers, and 3 sets of fluid and tubing detectors.

The size of the cell mass is minimized by increasing the concentration ratio (CR) as far as possible. CR is the ratio of the rate of unwashed undiluted cell volume coming into the spinning membrane filter to the rate of washed cell volume exiting the spinning membrane filter. In the wash circuit, there are four variables to control CR, the recirculation rate (r), the buffer solution rate (b), the cell source rate (c), and the filtrate rate 6f. The relationship is c+b=r+f, and CR=c/r=1+(f−b)/r.

For both the Isolex® 300i and the Stand-alone system, the cells are concentrated and washed automatically. We have found that by concentrating, diluting, and concentrating again multiple times, the volume can be more consistently controlled. Thus, between every other cell product cycle through the spinner (i.e., spinning membrane filter) the cell volume is diluted and reconcentrated. If the number of cycles left is predicted to be less than 2.5 cycles, the dilutions stop. During dilutions, the filtrate pump P4 is stopped, the buffer pump P2 runs at a fixed rate and the recirculation pump P3 runs at about 110% of the buffer rate. This allows the membrane to be rinsed and dilutes the cell concentrate through the port with the more concentrated cells.

The transmembrane pressure is regulated by controlling the concentration ratio CR using the recirculation pump P3. The concentration ratio CR is controlled to a target pressure by a PID (Proportional/Integrative/Derivative) control through the pressure measurements. The pressure measurements are taken from the pressure transducer connected to the filtrate line and are adjusted for the centrifugal effects on the fluid to yield a trans-membrane pressure. If the bag volume drops below the target volume, CR is no longer the controlling parameter. Instead, the scale weight is controlled by the buffer pump P2 and CR is calculated as: CR=c/r. Given CR, the recirculation rate is calculated as r=70/CR−1 where CR is limited to>=2.

Filtrate rate (f) is set to its maximum in order to minimize the time to process the cells. Filtration pressure is an indicator of the concentration of blood cells along the membrane of the spinning membrane filter. However, if either the spinner 6, buffer pump P2 or recirculation pump P3 are not up to speed, the filtrate rate is reduced. The ratio of the measured spinner 6, buffer pump, or recirculation pump rate to the respective commanded rate is calculated. The filtrate rate is then calculated as $f_1 = \frac{3}{4}*MRR*TFR + \frac{1}{4}*TFR$, where $f_1$ is the minimum ratio adjusted rate to be commanded in ml/min, MRR is the minimum rate ratios described above, TFR is the target filtrate rate (70 ml/min). The filtrate rate is further reduced when the pressure error ($E_p$) described above is less than −5 mmHg. When this condition is true the filtrate rate is set to $f_2=f_1+E_p+5$, where $f_2$ is the final command filtrate rate and $f_1$ is the minimum ratio adjusted filtrate rate described above. During dilutions, the filtrate rate is set to 0.

Recirculation rate (r) is the primary regulating variable. The buffer solution rate (b) is used to regulate the concentration ratio CR between values of 1 and 2. The buffer pump P2 provides the primary regulation to the scale weight management control. When the Isoflow™ bag 5 fluid volume weight drops below the target (20–35 ml), the buffer is commanded to about 78 mmin. This is approximately 8 ml/min faster than the filtrate pump P4. This causes the bag weight to rise. Once the weight rises about 5 ml, the buffer once again becomes secondary to the concentration ratio control, the buffer pump P2 is regulated according to the equation $$b=(70+f)/2-r*(CR-1).$$

Because the blood cells can be damaged by stress, the controller automatically adjusts the rotor spin rate of the spinning membrane filter. As the recirculation rate (r) is decreased the exposure time of the cells in the spinning membrane filter increases as follows: t=v/(r+f), where t and v are time and volume, respectively, in the spinning membrane. When r slows, stress on the cells increases. The controller counteracts this by decreasing the spin rate linearly when r is reduced.

The amount of washing is based on an estimate of "residual". The residual represents the target component for reduction (e.g., platelets, antibody). This estimate is made possible by the mixing properties of the IsoFlow™ bag. The estimate is calculated similar to how serial dilutions would calculate the residual. However, it is recalculated several times a second. The equation is $$FSR_i=FSR_{i-1}-(F_i/(B_i+C_i)\times(C_i/V_i)\times FSRW_{i-1}\times TA)$$

where i=the discrete time interval $FSR_i$=Fraction of Starting Residual at time $t_i$ $FSR_{i-1}$=Fraction of Starting Residual at time $t_{i-1}$ $F_i$=Filtrate volume moved at rate f measured at time interval i−1 to i in units of ml $B_i$=Buffer volume moved at rate b measured at time interval i−1 to i in units of ml $C_i$=Cell source moved at rate c measured at time interval i in units of ml, including the rate from the IsoFlow™ bag 5, as well as the rate of addition of unwashed cells, if any, in same units $V_i$=cell product volume at time interval i in ml TA=Target Admittance The Target Admittance is the unitless constant that represents the ease with which a given substance passes through the membrane (the inverse of membrane impedance). For platelet wash the Target Admittance has been found to be between 0.5 and 1.0 with a preferred setting of 0.7. For antibody and release agent wash the Target Admittance has been found to be between 0.7 and 1.2 with a preferred setting at 1. The optimal level for the antibody used for CD34+ selection on the Isolex® 300i has been found to be in the range of 50–150 micrograms.

An estimate of the average number of times a cell has been through the spinning membrane acts as a backup for determining when to end a wash. Cell cycles are estimated based on the following equation:

$$\text{Cell cycles}_i=\int(R_j+F_j-B_j)/V_j=\int C_j/V_j$$

where $R_j$=Recirculation volume moved at rate r measured at time interval j in units of ml, and Cell cycles$_i$=Number of cycles through the spinning membrane device that the cell product has experienced at time interval i.

What is claimed is:

1. A method of recirculation washing of blood cells, comprising:

utilizing a flexible plastic recirculation wash bag or reservoir having a top port and a bottom port in conjunction with a spinning membrane filter having an inlet port for a diluted suspension of blood cells in buffer solution, a first outlet port for filtrate and a second outlet port for a concentrated suspension of blood cells in buffer solution, preferentially withdrawing a less dense suspension of blood cells in buffer solution from the recirculation wash bag through the top port, mixing the suspension with additional buffer solution to form a diluted suspension of blood cells in buffer solution, feeding the diluted suspension into the spinning membrane filter through the inlet port, withdrawing filtrate comprising buffer solution from the spinning membrane filter through the first outlet port, withdrawing a concentrated suspension of blood cells in buffer solution from the spinning membrane filter through the second outlet port, feeding the concentrated suspension into the bag through the bottom port, and continuing the recirculation washing until the desired amount of washing has been achieved.

2. The method of claim 1 wherein the suspension of blood cells withdrawn through the top port of the recirculation wash bag is mixed with unwashed blood cells as well as buffer solution before feeding the diluted suspension into the spinning membrane filter.

3. The method of claim 2 wherein the unwashed blood cells include platelets, the filtrate comprises a suspension of platelets in buffer solution, and the recirculation washing is continued until the platelet content of the concentrated suspension of cells has been reduced to the desired level.

4. The method of claim 1 wherein the recirculation wash bag at the beginning of the recirculation wash procedure contains, in addition to blood cells, an antibody which specifically bind an antigen on certain of the blood cells, wherein the filtrate comprises a suspension of the antibody in the buffer solution, and wherein the recirculation washing continues until the concentrated suspension of cells contained a desired level of unbound antibody.

5. The method of claim 1 wherein washing is continued until the fraction of starting residual has reached a predetermined value as determined by the equation:

$$FSR_i = FSR_{i-1} - (F_i/(B_i+C_i) \times (C_i/V_i) \times FSR_{i-1} \times TA)$$

where i=the discrete time interval

FSRi=Fraction of Starting Residual at time $t_i$ $FSR_{i-1}$=Fraction of Starting Residual at time $t_{i-1}$ $F_i$=Filtrate volume moved at ratef measured at time interval i–1 to i in units of ml $B_i$=Buffer volume moved at rate b measured at time interval i–1 to i in units of ml $C_i$=Cell source moved at rate c measured at time interval i in units of ml, including the rate from the recirculation wash bag, as well as the rate of addition of unwashed cells, if any, in same units Vi=cell product volume at time interval i in ml TA=Target Admittance, and residual is the component which the cell washing is targeted to reduce.

6. The method of claim 1 wherein at relatively large volumes or relatively slow flow rates, the step of preferential withdrawing a less dense suspension of blood cells allows sedimentation of larger cells in the recirculation wash bag and aids in reducing the cell concentration at the top port.

7. The method of claim 6 wherein the most washed and most concentrated cells are at the bottom region of the recirculating wash bag and the least washed and the least concentrated cells are at the top region of the recirculation wash bag.

8. The method of claim 1 wherein the step of preferential withdrawing a less dense suspension of blood cells aids in maximizing a concentration ratio (CR).

9. The method of claim 1 further comprising the step of providing the recirculation wash bag with an integral coarse filter having a tube of semi-rigid plastic mesh extending from the top port into the recirculation wash bag.

10. The method of claim 1 further comprising the step of providing the recirculation wash bag with a bubble trap at the top of the bag, and wherein the bubble trap has a plastic tubing extending into the bag from the top port.

11. The method of claim 1 further comprising the step of providing the recirculation wash bag with an integral coarse filter having a tube of semi-rigid plastic mesh extending from the top port into the recirculation wash bag and having a closed bottom end, and further comprising the step of providing the recirculation wash bag with a bubble trap at the top which comprises a plastic tubing extending from the top port into the recirculation wash bag inside the mesh tube.

12. The method of claim 11 wherein the mesh is sufficiently rigid that, when vacuum is pulled on the bag, causing it to collapse, the mesh tube holds an open path in the bag, so that blood cells in a buffer solution entering the bottom port can move up to the top port.

13. The method of claim 1 which includes other bags and associated tubing for use in a magnetic cell selection instrument, including a bag for antibody suspension in buffer, a bag for peptide release agent solution in buffer, a bag for a suspension of selected cells in buffer solution, and a bag for a suspension of non-selected cells in buffer solution.

14. A method of washing of blood cells comprising:

providing a reservoir having a first port and a second port, the first port being disposed in an upper region of the reservoir and the second port being disposed in a lower region of the reservoir;

withdrawing an amount of blood cell suspension from the reservoir through the first port, the withdrawn amount of blood cell suspension being less dense than the blood cell suspension located in a lower region of the reservoir;

introducing the withdrawn amount of blood cell suspension to a filter;

withdrawing a concentrated suspension of blood cells from the filter; and directing the concentrated suspension of blood cells from the filter into the reservoir through the second port.

15. The method of claim 14 further comprising:

repeating the aforesaid steps until the desired amount of washing has been achieved.

16. The method of claim 14 wherein the filter into which the withdrawn amount of blood cell suspension is introduced is a spinning membrane filter.

17. The method of claim 14 wherein the withdrawn amount of blood cell suspension is diluted with a buffer solution prior to introducing the withdrawn amount of blood cell suspension into the filter.

18. The method of claim 17 wherein washing is continued until the fraction of starting residual has reached a predetermined value as determined by the equation:

$$FSR_i = FSR_{i-1} - (F_i/(B_i+C_i) \times (C_i/V_i) \times FSR_{i-1} \times TA)$$

where i=the discrete time interval

FSRi=Fraction of Starting Residual at time $t_i$ $FSR_{i-1}$=Fraction of Starting Residual at time $t_{i-1}$ $F_i$=Filtrate volume moved at ratef measured at time interval i–1 to i in units of ml $B_i$=Buffer volume moved at rate b measured at time interval i–1 to i in units of ml $C_i$=Cell source moved at rate c measured at time interval i in units of ml, including the rate from the reservoir, as well as the rate of addition of unwashed cells, if any, in same units Vi=cell product volume at time interval i in ml TA=Target Admittance, and residual is the component which the cell washing is targeted to reduce.

19. The method of claim 14 wherein a filtrate is withdrawn from the filter at the same time the concentrated suspension of blood cells is withdrawn from the filter.

20. The method of claim 19 wherein the unwashed blood cells include platelets, the filtrate comprises a suspension of platelets in buffer solution, and the washing is continued until the platelet content of the concentrated suspension of cells has been reduced to the desired level.

21. The method of claim 19 wherein the reservoir at the beginning of the washing procedure contains, in addition to blood cells, an antibody which specifically binds an antigen on certain of the blood cells, which the filtrate comprises a suspension of the antibody in the buffer solution, and the washing continues until the concentrated suspension of cells contains a desired level of free of excess, unbound antibody.

22. A method of washing of blood cells comprising:

(a) providing a recirculation reservoir having a first port and a second port, the first port being disposed in an upper region of the reservoir, and the second port being disposed in a lower region of the reservoir;

(b) withdrawing an amount of blood cell suspension from the reservoir through the first port;

(c) introducing the withdrawn amount of blood cell suspension to a filter;

(d) withdrawing a concentrated suspension of blood cells from the filter; and (e) introducing the concentrated suspension of blood cells from the filter into the reservoir through the second port such that a cell density gradient is created in the reservoir whereby a more dense suspension of blood cells is located in the lower region and a less dense suspension of blood cells is located in the upper region of the reservoir;

wherein the cell density gradient is changed according to further introduction of a concentrated suspension of blood cells from the filter into the reservoir through the second port at a predetermined flow rate.

23. The method of claim 22 further comprising repeating steps (b) through (e).

24. The method of claim 22 wherein at relatively low volumes or relatively high flow rates, the step of introducing the concentrated suspension of blood cells into the reservoir through the second port causes mixing of larger cells in the reservoir and aids in providing a homogenous intercellular fluid at the second port.

25. The method of claim 22 wherein the filter into which the withdrawn amount of blood cell suspension is introduced is a spinning membrane filter.

26. The method of claim 22 wherein the withdrawn amount of blood cell suspension is diluted with a buffer solution prior to introducing the withdrawn amount of blood cell suspension into the filter.

27. The method of claim 22 wherein a filtrate is withdrawn from the filter at the same time the concentrated suspension of blood cells is withdrawn from the filter.

28. The method of claim 27 wherein the unwashed blood cells include platelets, the filtrate comprises a suspension of platelets in buffer solution, and the washing is continued until the platelet content of the concentrated suspension of cells have been reduced to the desired level.

29. The method of claim 27 wherein the reservoir at the beginning of the washing procedure contains, in addition to blood cells, an antibody which specifically binds an antigen on certain of the blood cells, which the filtrate comprises a suspension of the antibody in the buffer solution, and the washing continues until the concentrated suspension of cells contains a desired level of unbound antibody.

30. The method of claim 2, further comprising:

minimizing a volume of blood cell suspension by maximizing a concentration ratio (CR), the CR ratio being a ratio of the rate of unwashed, undiluted cell volume entering the spinning filter to a rate of washed cell volume exiting the spinning membrane filter.

31. The method of claim 30, further comprising:

determining the concentration ratio (CR) by controlling four variables: a recirculation rate (r), a buffer solution rate (b), a cell source rate (c), and a filtrate rate (f).

32. The method of claim 31, wherein the relationship between the four variables is $c+b=r+f$ and $CR=c/r=1+(f-b)/r$.

33. The method of claim 25, further comprising:

minimizing a volume of blood cell suspension by maximizing a concentration ratio (CR), the CR ratio being a ratio of the rate of unwashed, undiluted cell volume entering the spinning membrane filter to a rate of washed cell volume exiting the spinning membrane filter.

* * * * *

UNITED STATES PATENT AND TRADEMARK OFFICE
CERTIFICATE OF CORRECTION

PATENT NO. : 6,251,295 B1
DATED : June 26, 2001
INVENTOR(S) : Craig L. Johnson

It is certified that error appears in the above-identified patent and that said Letters Patent is hereby corrected as shown below:

Column 11,
Line 52, -- $FSR_i = FSR_{i-1} - (F_i/(B_i + C_i) \times (C_i/V_i) \times FSR_{i-1} \times TA)$ --

Column 13,
Line 1, -- $FSR_i = FSR_{i-1} - (F_i/(B_i + C_i) \times (C_i/V_i) \times FSR_{i-1} \times TA)$ --
Line 5, -- $F_i$ = Filtrate volume moved at rate f measured at time --

Column 14,
Line 26, -- $F_i$ = Filtrate volume moved at rate f measured at time --

Signed and Sealed this

Twelfth Day of March, 2002

*Attest:*

*Attesting Officer*

JAMES E. ROGAN
*Director of the United States Patent and Trademark Office*